United States Patent [19]

Urist

[11] Patent Number: 4,857,456
[45] Date of Patent: Aug. 15, 1989

[54] ASSAY OF BONE MORPHOGENETIC PROTEIN (BMP) AND ANTI-BMP ANTIBODY FOR THE DIAGNOSIS OF BONE DISORDERS

[75] Inventor: Marshall R. Urist, Pacific Palisades, Calif.

[73] Assignee: The Regents of the University of California, Berkeley, Calif.

[21] Appl. No.: 728,774

[22] Filed: Apr. 30, 1985

[51] Int. Cl.$^4$ ............... G01N 33/535; G01N 33/68; G01N 33/543
[52] U.S. Cl. ............... 435/7; 436/518; 436/547; 436/811; 436/86
[58] Field of Search ............... 530/387, 388, 356; 435/7, 810, 4; 424/9; 436/518, 501, 547, 548, 808, 810, 811, 815, 86

[56] References Cited

PUBLICATIONS

Urist et al., Normal and Abnormal Bone Growth: Basic and Clinical Research, 877–96 (1985).
Urist et al., Proc. Soc. Exp. Biol Med. 176(4), 472–5 (1984) Chemical Abstract 101:128399h.
Urist et al., Science, vol. 220, pp. 680–686 (1983).

Primary Examiner—Esther M. Kepplinger
Attorney, Agent, or Firm—Kenyon & Kenyon

[57] ABSTRACT

Method for diagnosing bone disorders comprising assaying bone morphogenetic protein (BMP) or anti-bone morphogenetic protein (anti-BMP) antibody in body fluids. The diagnosis may be carried out by comparing the BMP, anti-BMP antibody or the ratio of the two to normal assay standards. A diagnostic kit for accomplishing these methods is described.

48 Claims, 3 Drawing Sheets

ASSAY OF BONE MORPHOGENETIC PROTEIN (BMP) AND ANTI-BMP ANTIBODY FOR THE DIAGNOSIS OF BONE DISORDERS

This invention was made with Government support under Grant No. DE 02103-20 with the National Institutes of Health and the University of California. The Government has certain rights in this invention.

FIELD OF INVENTION

This invention relates to novel methods for clinically diagnosing bone disorders. More particularly, bone morphogenetic protein (BMP) which was previously discovered in bone tissue has been discovered to be present in body fluid, in serum, and is assayable by displacement method of radioimmunoassay (RIA) and enzyme-linked immunosorbent assay (ELISA). Quantitative measurements of BMP in serum or anti-BMP antibody are diagnostic of bone health or disease.

BACKGROUND AND SUMMARY OF THE INVENTION

Applicant has previously discovered and isolated an agent from bone tissue capable of inducing bone formation when implanted in tissue cells. The inductive agent has been named bone morphogenetic protein, designated BMP. See, U.S. Pat. No. 4,294,753; U.S. Pat. No. 4,455,256; and pending Application Ser. No. 523,606, filed Aug. 16, 1983, that are incorporated herein by reference.

Applicant also has discovered and produced from bone tissue related inductive agents: bone morphogenetic peptides (BMP-p) and bone morphogenetic protein polypeptide (BMPP). BMP-p are smaller peptides containing the functional and immunoreactive domain of BMP. BMPP is a lower molecular weight bone morphogenetic agent that is believed to be a subunit of BMP.

The biochemical mechanism by which the BMP family of agents induces bone formation is not known. However, the process has been classified as phenotypic transformation, as distinguished from malignant transformation by a carcinogen. Phenotypic transformation is a self-limited host-regulated development process. BMP agents induce bone to develop de novo in extraskeletal sites by differentation of perivascular connective tissue pericytes.

The discovery by applicant of BMP agents heralds a new era in the treatment of many bone disorders. When exogenous BMP was implanted in a fracture, or surgical bone defects, repair of the bone rapidly occurred within a few months. It is expected that BMP-induced de novo synthesis of bone tissue will replace many types of bone transplant operations. Present and future applications of BMP implants cover all forms of bone disorders.

The present invention relates to the diagnosis of bone disorders based upon applicant's discovery that even though BMP had been isolated from bone and classified as a paracrine rather than an endocrine agent, BMP is quantitatively detectable in serum by assay methods such as radioimmunoassay (RIA) and enzyme-linked immunosorbent assay (ELISA). Urist, M. R., Hudak, R. T., Radioimmunoassay of Bone Morphogenetic Protein in Serum: A Tissue-Specific Parameter of Bone Metabolism, *Pro Soc Exp Biol Med.*, 176:472-475 (1984). BMP was found in sera of normal adult subjects unimplanted with exogenous BMP. Without intending to be limited by theory, the working hypothesis is that BMP is a normal by-product of bone metabolism, and it now has been found that assaying the concentration of serum BMP or anti-BMP antibody is diagnostic of bone health or disease.

BMP RIA and BMP ELISA values were higher in rapidly growing children with normally high levels of bone turnover than in non-growing adults with normally low rates of bone turnover. Patients with extensive Paget's disease showed very high levels of serum BMP. The range of BMP values in patients with osteosarcoma was about the same as observed in rapidly growing children. Women with osteoporosis had serum BMP mean values that were about 10-11% that in normal premenopausal women. BMP RIA mean values in non-osteoporotic post menopausal women were within the range observed in normal premenopausal women.

Alkaline phosphatase, a ubiquitous enzyme, is the time-honored chemical laboratory indicator of the level of osteoblastic activity. Alkaline phosphatase levels are generally elevated in adults with Paget's disease and some types of osteosarcoma, conditions characterized by increased osteoblastic activity associated with increased bone turnover. In osteoporosis in postmenopausal women, in whom alkaline phosphatase levels are generally normal, the levels of serum BMP were low. Thus in osteoporosis, a disease for which there is no presently known laboratory method of diagnosis, serum BMP determinations were more useful than alkaline phosphatase for early detection of osteoporosis.

Another novel method for diagnosing bone disease also has been developed. Assaying the concentration of anti-BMP antibody in serum, or the ratio of serum BMP:anti-BMP antibody, is diagnostic of bone health or disease.

Based on the present invention, a commercially feasible diagnostic kit for diagnosing bone disorders can be designed comprising means for assaying BMP or anti-BMP antibody in body fluids.

DETAILED DESCRIPTION OF INVENTION

BMP was detected in serum and quantitative assay of serum BMP concentration was diagnostic of bone disorders. Quantitative assay of BMP concentration in other body fluids, such as urine, can be diagnostic of bone disorders.

The two assay systems selected to detect and assay concentration of serum BMP were standard displacement radioimmunoassay (RIA) and enzyme-linked immunosorbent assay (ELISA). Other assay systems for body fluids can be employed to practice the invention. Example I below is an embodiment of the invention using RIA; Example II below is an embodiment of the invention using ELISA.

Quantitative assay of the concentration of anti-BMP antibody in serum, or the ratio of serum BMP:anti-BMP antibody, was diagnostic of bone disorders. An embodiment of this invention is example III below.

EXAMPLE I

BMP-RIA

Figure 1:
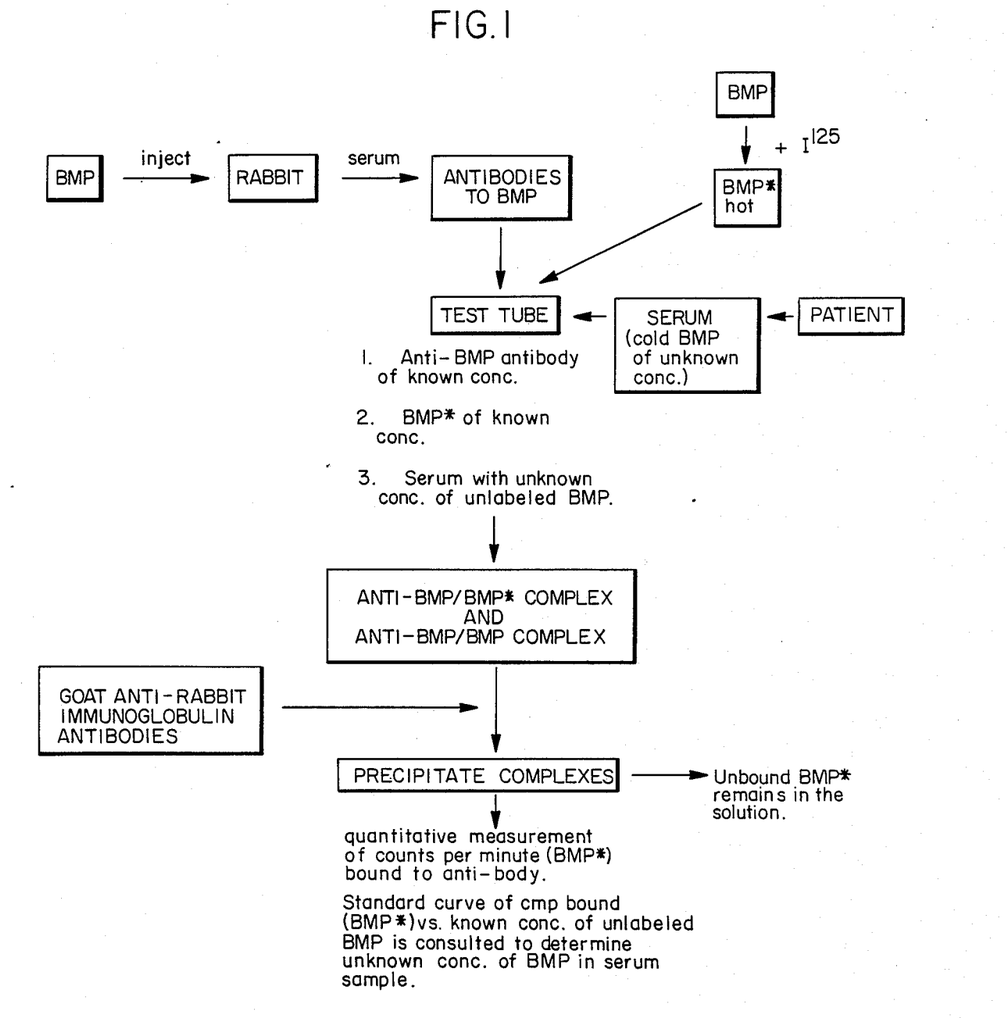

Radioimmunoassay (RIA) is a sensitive procedure for quantitative in vitro measurement of drug and hormone levels in biological fluids. RIA is based upon the observation that unlabeled antigen and radioactive-labeled antigen compete to bind with antibody to the antigen in vitro. The essence of the BMP-RIA as embodied in the present invention was that unlabeled BMP and radioactively labeled BMP (BMP*) competed to bind with anti-BMP antibodies in an in vitro reaction mixture. See Figure I. All reaction mixtures, whether for standard curve construction or for serum sample assays, contained set amounts of BMP* and anti-BMP antibodies, and a variable amount of BMP (standards or serum samples). The anti-BMP antibodies bound either with BMP or BMP*, and the binding of BMP* was dependent upon the amount of unlabeled BMP present. As the amount of BMP in the reaction mixture increased, the amount of BMP* that bound to the available anti-BMP antibody decreased.

To assay the concentration of BMP in serum, reaction mixtures were set up containing BMP*, anti-BMP antibody and serum sample. The amount of BMP* bound to anti-BMP antibody was measured (in counts per minute), and the amount of BMP present was determined from a standard curve. A standard curve was constructed by experimentally determining that when "X" amount of unlabeled BMP standard was introduced into the reaction, "A" cpm (BMP*) were recovered bound to anti-BMP antibody; and when "Y" amount of unlabeled BMP was introduced into the reaction, "B" cpm were recovered bound to anti-BMP antibody; and etc. From this data, a standard curve was constructed showing cmp (BMP*) recovered bound to antibody versus unlabeled BMP present. Subsequently, when a serum sample with unknown amount of BMP was assayed in the reaction mixture, and "A" cpm were recovered bound to anti-BMP antibody, it was determined from the standard curve that "X" amount of BMP was present in the serum sample.

In this embodiment of the invention, purified bovine BMP was used to produce rabbit anti-bovine BMP antibodies and radioactively labeled bovine BMP*. Human BMP bound to rabbit anti-bovine BMP antibodies to the same extent as did bovine BMP*. In an assay test tube containing rabbit anti-bovine BMP antibodies, human BMP in a serum sample and bovine BMP*, the human BMP and the bovine BMP* competed to bind to the available anti-BMP antibodies. The rabbit anti-bovine BMP antibodies with bound human BMP or bound bovine BMP* were precipitated with goat antibody to rabbit immunoglobulins and counts per minute (cpm) were determined. The fewer cpm (bovine BMP*) recovered bound to the antibodies, the greater the concentration of human BMP in the serum sample, which concentration was quantitatively determined from the standard curve.

The detailed procedure for the quantitative assay of BMP in serum by RIA was as follows:

Preparation of unlabeled antigen (BMP)—BMP was prepared from bovine cortical bone and purified by methods previously described in detail. Reference is made to Pat. No. 4,294,753; Pat. No. 4,455,256; and pending Application Ser. No. 523,606, filed Aug. 16, 1983, the disclosures of which are incorporated herein by reference. See also: Urist, M.R., et al., *Proc. Soc. Exp. Biol Med.*, 173:194-199, 1983; and, Urist, M.R., et al., *Proc. Natl. Acad. Sci.* (USA) 81:371-375, 1984. Bovine BMP cross reacts with human BMP.

Preparation of antibodies.—An antibody to unlabeled BMP antigen was prepared by injection of purified bovine BMP into rabbits, 5 mg/kilo of rabbit, in Freund's adjuvent, as a 5 mg/ml solution, subcutaneously per week for 3 weeks. The serum was collected 3 days after the last injection.

Iodination of BMP (BMP*).—BMP was iodinated using a modification of the method of Hunter and Greenwood. Hunter W. M., Greenwood F.C., Preparation of Iodine 131 labelled human growth hormone of high specific activity, *Nature* 194:495-496, 1962, incorporated herein by reference. To 10 ul (microliters) of BMP in 50 ul phosphate buffered saline (PBS) pH 7.0, were added 4 uCi (microcuries) of $^{125}I$ (Amersham) and 10 ul of chloramine T (5mg/12.5ml of solution). The reaction was allowed to continue for 180 seconds and terminated with the addition of 10 ul sodium metabisulfite (5mg/10ml of solution). This product was then purified on a 0.7×25 cm column of Sephacryl S-200 (Pharmacia, Piscataway, New Jersey) using 0.1 M PBS, pH 6.55, containing 0.05% Tween 20.

Procedure.—A 200 ul sample of patient serum or known BMP standards were added to the tubes followed by 100 ul of anti-BMP and 100 ul of $^{125}I$-BMP yielding 20,000 counts per minute (cpm). The standards were run at concentrations of 2, 5, 10, 50, 100, 200, and 500 ng/ml. Standards, anti-BMP antibody and $^{125}I$-BMP were combined in a 0.1 M phosphate buffered saline, pH 7.6, containing bovine serum albumin, rabbit gamma globulin and N-ethylmaleimide. The assay of the serum sample or the known BMP standard was set up in duplicate in 12×75 mm borosilicate tubes. The tubes were vortexed and incubated for 2 days at 4° C. The anti-BMP antibody with bound BMP or BMP* was precipitated using the second antibody (goat anti-rabbit immunoglobulin) technique as follows. 100 ul of second antibody was added to each tube and allowed to incubate an additional hour at 4° C.; the tubes were then centrifuged at 1000 g for 15 minutes at 6° C. and were aspirated and then radioactively counted.

Immunoassay.—The samples of serum were analyzed both quantitatively and qualitatively by enzyme-linked immunosorbent assay (ELISA), using the dot immunobinding method. Hawkes R., Niday E., Gordon J., A dot-immunobinding assay for monoclonal and other antibodies, *An Biochem*, 19:142-147, 1982, incorporated herein by reference.

Serum BMP Analyses.—Eighty samples of normal human serum (0.5 ml) were collected from surplus human blood. Normal sera from six different children also was obtained. Sera from three patients with severe Paget's disease, two male and one female, (with very high levels of serum alkaline phosphatase), were prepared from blood collected for routine diagnostic studies. Sera also were prepared from blood of six patients with osteosarcoma and ten postmenopausal women with severe osteoporosis and ten women of comparable age without osteoporosis.

Control.—Three control analyses were performed on each sample to exclude unspecific protein reactions: (a) human serum stripped of protein hormones with dextran-coated charcoal (NORTI-SG Fischer Chem. Los Angeles, Calif.), (b) serum supplemented with 6 to 16 ng of prolactin, (c) serum supersaturated with 100 ng of prolactin.

Figure 2:
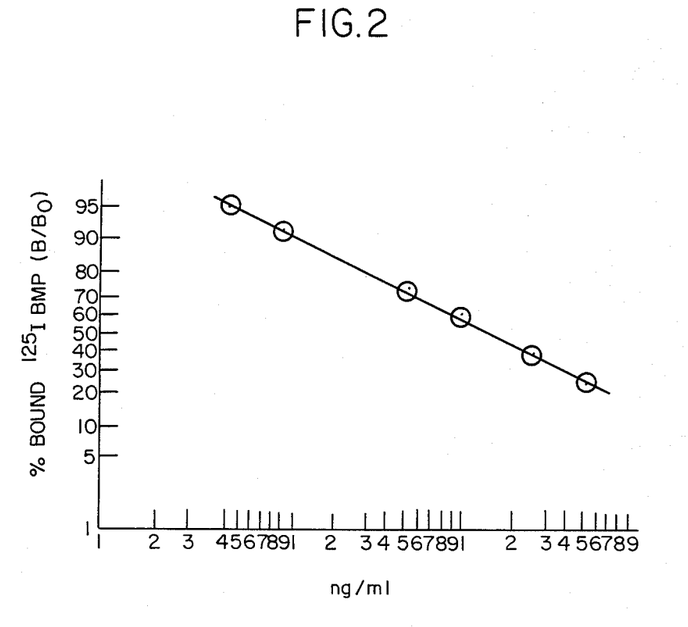

Standard Curve.—FIG. 2 shows a dose response curve of the RIA for BMP when plotted on a log-log scale. The concentration of BMP is plotted on the horizontal axis, while the percent bound BMP$^{125}I$ is plotted on the vertical axis as the ratio of B/Bo. "Bo" represents the maximum quantity of BMP$^{125}I$ bound to the antibody in the absence of non-radioactive BMP. "B" represents the amount of BMP$^{125}I$ bound to the antibody when known concentrations of non-radioactive BMP are present. In order to obtain maximum displacement, a 200 ul sample size was used.

To validate an RIA, one must show that the antigen used for the standards (bovine BMP) is immunologically identical to the material being measured in the serum (human BMP). Midgley, A. R., Jr., Niswender, G. D., and Rebar, R. W., Principles for the assessment of the reliability of radioimmunoassay methods (precision, accuracy, sensitivity, specificity), *Acta Endocrinol.*, 63 (Suppl):142.163. Skelly, D. S., Brown, L. P. and Besch, P. K., Radioimmunoassay, *Clin Chem* 19:146-186, 1973. Berson, S.A. and Yalow, R.S., In *Peptide Hormones*, S. A. Berson and R. S. Yalow Eds., Amsterdam, North Holland Publishing Co, pg. 84, 1973. Therefore, we used the parallelism and recovery methods.

Table I demonstrates the parallelism or effects of dilutions on the assay. Serial dilutions of two samples with a high concentration of BMP were made from 0 to 16 fold. If both standard and serum BMP are immunologically identical then the values obtained from a diluted sample multiplied by its dilution factor should be within experimental error, identical to the undiluted value. This is essentially the case.

TABLE I

| | Parallelism of BMP RIA | |
|---|---|---|
| Dilution | Exp A | Exp B |
| 0 | Value obtained | 370 | 160 |
| 1:2 | value obtained | 180 | 84 |
| | value (x) dil. factor | 180 × 2 = 360 | 84 × 2 = 168 |
| 1:4 | value obtained | 80 | 38 |
| | value (x) dil. factor | 40 × 4 = 320 | 38 × 4 = 152 |
| 1:8 | value obtained | 40 | 19 |
| | value (x) dil. factor | 40 × 8 = 320 | 19 × 18 = 152 |
| 1:16 | value obtained | 20 | 11 |
| | value (x) dil. factor | 20 × 16 = 320 | 11 × 16 = 176 |

All values are ng/ml BMP

Table II further demonstrates the accuracy of this BMP RIA by its capacity to detect the additive BMP concentrations. In experiment A with initial (baseline) value of 17 ng/ml, and B with 50 ng/ml, the total RIA values prove to be acceptably close to the sum of the initial values plus the added quantities of BMP, showing that the BMP used for the standards and the serum BMP must be immunologically identical.

TABLE II

| | Recovery of BMP RIA | | | |
|---|---|---|---|---|
| BMP Added, (ng) | Test A (17 ng/ml) | | Test B (50 ng/ml) | |
| | Expected | Recovered | Expected | Recovered |
| 250 | 267 | 280 | 300 | 320 |
| 125 | 142 | 150 | 175 | 190 |
| 50 | 67 | 64 | 100 | 90 |
| 25 | 42 | 38 | 67 | 72 |

All Values are ng/ml BMP.

In order to prove the precision or reproducibility of the assay, three samples were run in the beginning tubes and again at the end tubes of the assay on five different occasions. The data presented in Table III shows that the results are within an acceptable range for RIAs.

TABLE III

| BMP RIA Determinations Of Three Sets of Samples on Five Successive Days | | | |
|---|---|---|---|
| | ng/ml of BMP | | |
| | Serum A | Serum B | Serum C |
| | 10 | 21 | 17 |
| | 12 | 24 | 19 |
| | 11 | 25 | 20 |
| | 14 | 27 | 17 |
| | 10 | 25 | 16 |
| Mean: | 11.4 | 24.4 | 17.8 |
| Standard Deviation: | 1.67 | 2.19 | 1.64 |
| Coefficient of Variation, %: | 14.6 | 9.0 | 9 |

Table IV summarizes the results obtained by performing RIA on sera of rapidly growing normal children, normal adults, patients with Paget's disease, patients with osteosarcoma, postmenopausal women with severe osteoporosis, and women of comparable age without osteroporosis.

TABLE IV

| Conditions | No. patients | No. analyses | RIA, ng.ml | | |
|---|---|---|---|---|---|
| | | | Range | Mean | S.D. |
| Adult Male | 35 | 69 | 1–23 | 14.43 | 5.7 |
| Adult female Premenopausal | 45 | 100 | 13–35 | 18.20 | 4.4 |
| Children, yr., 2–8 | 6 | 9 | 20–72 | 56.0 | 18.9 |
| Paget's Disease | 3 | 5 | 121–250 | ND | 76.1 |
| Osteosarcoma pre and postop | 6 | 10 | 36–80 | 61.8 | 19.1 |
| Postmenopausal female, non-osteoporosis | 10 | 14 | 14–41 | 16.45 | 6.6 |
| Spinal severe Osteopososis, female ages 16–80 | 10 | 18 | 1–4.8 | 2.0 | 0.3 |

With the ELISA procedure, the mouse anti-human BMP cross-reacted 100% with both human and bovine BMP. Similarly, the rabbit anti-bovine BMP cross-reacted 100% with both the human and bovine BMP which demonstrates that either BMP is not species specific, or the segment of the molecule our antisera detects may be common to several species. On samples listed in Tables I to III with BMP RIA values greater than 15 ng/ml, the results were confirmed by an unequivocally positive qualitative ELISA.

The hypothesis supported by the data obtained from the above RIA procedure for BMP is that BMP is a normal by-product of local or paracrine bone metabolism that appears in the sera of normal individuals. BMP RIA values are higher in rapidly growing children with normally high levels of bone turnover than in nongrowing adults with normally low rates of bone turnover. Rapidly growing children have a range of at least 20 to 72 ng/ml, while normal adults show less than 16 ng. The standard deviation of the values for children was 18.9, compared with 5.7 and 4.40 for men and women, respectively, and was attributable to one child with a value of 20 ng/ml compared to 5 others with values ranging from 54 to 72 ng/ml. Three patients with extensive Paget's disease consistently show high levels, over 250 ng, of serum BMP.

The range of BMP RIA values in patients with osteosarcoma was about the same as observed in rapidly growing children. Three of the six patients were post amputation with the extent of tumor burden remaining in metastases not known. Two of the six patients had a relatively small tumor mass (2 cm³). One of the six with a large tumor (10 cm³) had had chemotherapy.

The women with osteoporosis selected for this study were above the age of 65, well in stage 3 of the disease, with 5 or more collapsed vertebra, and 2 to 4 inches loss of height. The BMP RIA mean values were about 10–11% of the mean value in normal premenopausal women. The BMP RIA mean values in ten control non-osteoporotic post-menopausal women were within the range observed in 45 normal women (ages 45 to 65). About 66 percent of the non-osteoporotic or "normal group" had spondylosis or osteoarthritis.

Example II

BMP-ELISA

Figure 3:
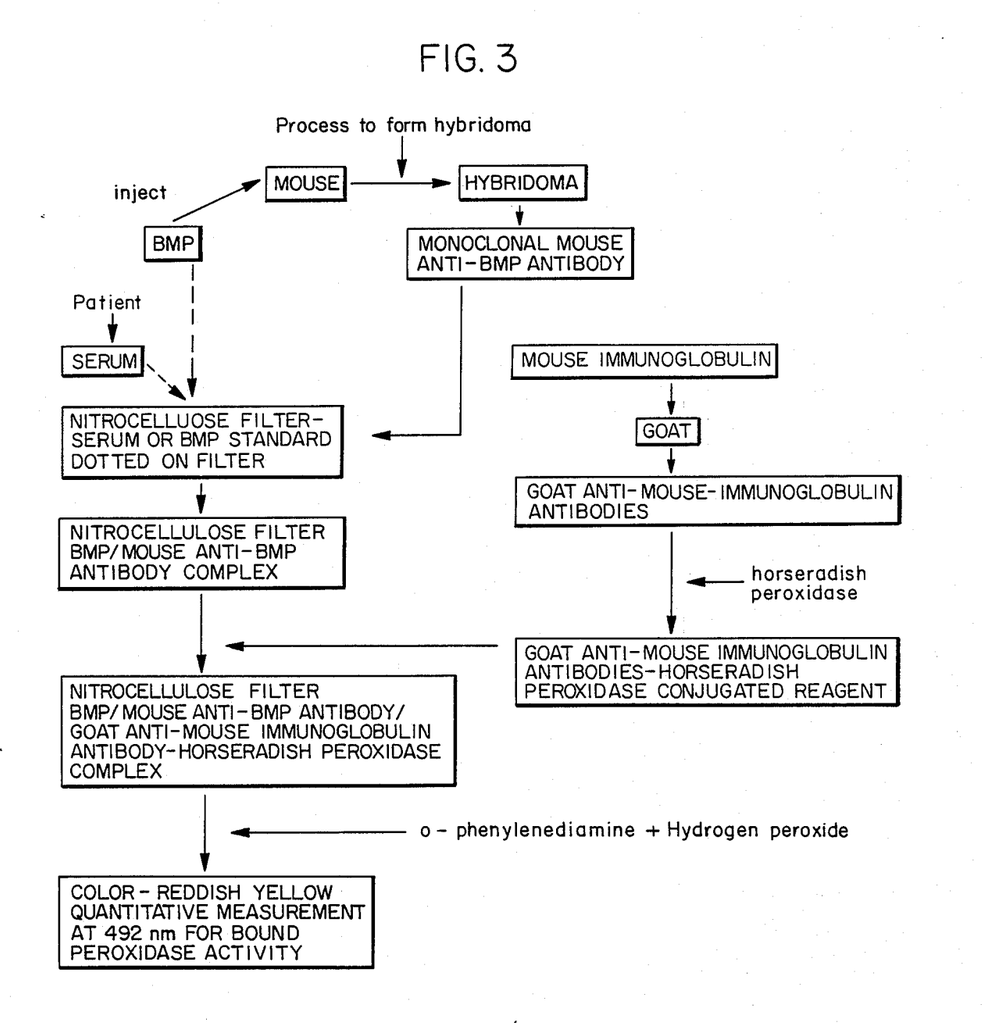

BMP in serum was detected and its concentration quantitatively assayed by enzyme-linked immunosorbent assay (ELISA) according to the method of Hawkes et al., cited below. See FIG. 3.

A hybridoma cell line secreting mouse monoclonal anti-BMP antibody was produced for use in the ELISA method. Other monoclonal or polyclonal antibodies to BMP can be employed in the ELISA method.

In this embodiment of the invention, the procedure for detecting and assaying BMP in serum by ELISA was performed by (1) dotting a nitrocellulose filter with a sample of serum containing unknown BMP concentration or a standard sample of BMP of known concentration, (2) incubating the sample fixed on the filter with mouse anti-BMP antibody purified from a hybridoma secreting monoclonal anti-BMP antibody, (3) incubating the BMP-anti BMP antibody complex formed on the filter with goat anti-mouse immunoglobulin horseradish peroxidase conjugated reagent, and (4) testing for bound peroxidase activity. The amount of bound peroxidase activity was proportional to the amount of bound anti-BMP antibody, which in turn was proportional to the amount of BMP in the serum sample. A standard curve of BMP concentration was constructed from which the unknown concentration of BMP in serum was determined.

The detailed procedure for the quantitative assay of BMP in serum by ELISA was as follows:

Production of hybridoma secreting monoclonal anti-BMP antibody. Bovine bone morphogenetic protein (bBMP) with relative molecular weight ($M_r$) 18.5k was purified by methods previously described. See, U.S. Pat. No. 4,294,753; U.S. Pat. No. 4,455,256; and pending Application Ser. No. 523,606, filed Aug. 16, 1983.

A 0.4 mg sample of purified BMP in 0.2 ml of phosphate buffered saline and 0.2 ml of Freund's adjuvant (complete) was injected subcutaneously into BALB/c mice. Nine days later, the spleen cells were fused with myeloma cell 653, a non secreting clone from P3X63Ag8 (American Type Culture Collection Rockville, MD), at a ratio of 4:1 with 50% polyethylene glycol by the methods of Kohler and Milstein. *Nature*, 1975, 256:496–497; *Eur. J. Immunol.*, 1976, 6:511–519. The culture media was RPM1 medium 1640 (Gibco, Grand Island New York, N.Y.). Supernatants were screened against $M_r$ 14k, 17k, 22k, 28k, and 18.5k bone matrix proteins by dot immunobinding test as described below. One hybrid, designated U-5, produced a discriminating antibody, exclusively against $M_r$ 18.5k BMP. The hybrid was repeatedly cloned by the limiting dilution method, and produced ascites fluid within 10 days after intraperitoneal injections into normal BALB/b mice. The U-5 antibody was shown to be IgM by Ouchterlony plate immunoprecipitation. U-5 anti-bBMP antibody was purified, as described below, by Sephacryl S-300 chromatography.

Procedure for Purification of anti-bBMP. Approximately 100 ml of ascites fluid was collected from 10 mice which had been injected with $2 \times 10^6$ U-5 hyrbidoma cells per mouse 10 days previously. The ascites fluid was diluted with 500 ml of phosphate buffered saline (PBS) and the protein salted out with 600 ml of saturated ammonium sulfate. After centrifugation at 15,000 RPM, the precipitate was washed in ½ saturated ammonium sulfate solution. The precipitate was redissolved in 5 ml PBS and the solution dialyzed in 10 volumes PBS, three times at 4° C. The retentate was applied to a Sephacryl S-300 column (2.5×100cm) and eluted with PBS solution (0.005 N phosphate, 0.15M NaCl, pH6.8). After dialysis against water and lyophilization, the sample was weighed for electrophoretic analysis. The purity of the U-5 IgM anti-BMP was determined by comparing the sodium dodecyl sulfate (SDS) polyacrylaminde gel electrophoresis (PAGE) pattern with a commercially available IgM (Chemicon, Los Angeles, Ca). The purified U-5 material consisted of two major components. The U-5 anti-BMP was less contaminated than the commercial IgM..

Procedure for assay of human BMP in serum. An immunoassay system was employed with U-5 anti-BMP antibody according to the method of Hawkes R, Niday E, Gordon J., A dot-immunobinding assay for monoclonal and other antibodies, *Anal Biochem.*, 119:142–147, 1982, herein incorporated by reference.

A. Dot immunoassay—By means of "dot" solid state method it is possible to select the best dilution or range of concentration for an accurate analysis of unknown values in serum.

The following bone matrix proteins are closely associated with BMP, and identified by $M_r$ of 22k, 28k, 34k, and 14k. One of these matrix proteins or bovine serum albumin (BSA) used as antigen for the control test. The BMP or the control non-BMP antigen was weighed and dissolved in Tris buffered saline (pH 7.4) in various dilutions ranging from 500 ug/ml to $10^{-4}$ dilution. 1 ul of each dilution was dotted onto a nitro-cellulose filter (millipore HA, 0.34 um pore size). After blocking in a 3% BSA medium, the paper was incubated with purified U-5 anti-BMP antibody (110 ug/ml) and then with goat anti-mouse immunoglobulin (GAMIg)-horseradish peroxidase conjugated reagent designed to detect mouse immunoglobulins. The complex was incubated in 4-chloro-1-naphthol and hydrogen peroxide to develop color. A positive reaction was observed as a dark blue colored spot against the white background.

B. Quantitative Micro-ELISA test. The antigen was immobilized by dot on the nitrocellulose paper and the procedure followed as described above except that the o-phenylenediamine (OPD) was used as a substrate. The positive reaction was read as reddish-yellow color at 492 nm on a micro-ELISA minireader (Dynatech, Alexandria, VA 22314).

For both dot and micro ELISA, each assay was calibrated by dilutions of a standard purified BMP ($M_r$ 18.5k) for reference to accurately analyze a series of unknown samples. Three blanks or negative controls were set up. The first were wells to which no target antigen (BMP) was added. These wells contained blocking protein only: an irrelevant protein (i.e., 34k or 14k) to which the antibody does not react; a negative serum or sample absorbed anti-BMP but responded only as any non-specific protein binding to the developing system. The second negative controls were in wells in which no first antibody was added or in which an irrelevant monoclonal antibody of the same isotype as the first antibody was added; these controls were for non-specific binding of the developing antibody or for non-specific binding of the first antibody respectively. The third controls were wells to which no second antibody was added: this control is important in the ELISA test to control extraneous peroxidase activity in serum. Each assay was performed with negative controls and BMP test solutions for construction of a BMP standard curve with a range of 10 to 130 ng/ml.

A standard curve was prepared showing the relationship between concentration of protein and quantity of BMP detected in Tris buffered saline solutions by the micro ELISA colorimetic method. A linear relationship with respect to BMP was obtained in the range of 2 to 38 ng. At designated dilution determined by the dot method, and optical densities between 0.8 and 0.9, 40 to 80 ng were detected. The amount detected reached a plateau of 80 to 130 ng/ml showing that the solution must be diluted to carry out the analysis within the range of 10 to 40 ng/ml.

C. Assay for Serum $M_r$ 18.5K BMP. Serum obtained from normal subjects and patients with bone disease was diluted two fold or from $10^{-1}$ to $10^{-5}$ as required. One ul of each dilution was applied to dots on nitrocellulose paper, and the space then blocked with 3% BSA. The paper was finally immersed in a solution of the blocking medium containing 110 ug/ml of purified anti-BMP. After incubating for 12 hours at 28° C., the paper was washed three times with Tris buffer in saline pH 7.4 for 30 minutes. The washed paper was placed in peroxidase labeled affinity purified antibody to human IgG + IgM (H+L) (goat anti-mouse serum absorbed second antibody) for 2 hours (diluted with blocking medium 1:500) at 28° C., and rewashed three times with Tris buffered in saline. 4-Cl-1-naphthol was used as a substrate for dot ELISA test and OPD for micro-ELISA. Each assay included a standard curve in dilutions corresponding to the serum dilution. The use of mouse U-5 anti-bovine BMP antibody (anti-bBMP) to detect human BMP (hBMP) is based on the fact that the U-5 anti-bBMP cross reacts strongly with human BMP.

The ELISA results obtained on normal and abnormal subjects were compared with results obtained by displacement $^{125}I$ BMP RIA, and tabulated in Table V.

TABLE V

| | Relative Values RIA and ELISA of BMP | | | |
|---|---|---|---|---|
| Subject | No. Patients | Sex | RIA ng/ml | ELISA ng/ml |
| Adults | 8 | M | 1–23(70) | 4–28(66) |
| | 52 | F | 13–35(88) | 15–39(100) |
| Children | 10 | | 20–72(16) | 30–78(20) |
| Paget's Disease | 6 | | 45–300(10) | 60–300(10) |
| | 2 | M | 105–300(4) | |
| | 4 | F | 35–258(6) | |
| Osteosarcoma | 10 | | 28–130(20) | 36–212(12) |
| | 4 | M | 28–130(10) | 38–150(8) |
| | 6 | F | 35–52(10) | 40–61(8) |
| Osteoporosis | 10 | | 1–8(14) | 2–9(12) |

EXAMPLE III

Anti-BMP antibody

Another method of diagnosing bone disorders is by quantitative measurement of anti-BMP antibody levels in serum. The procedure used to assay human serum anti-BMP antibody by ELISA was as follows:

A. Dot Immunoassay. 1 ul of soluble BMP, 0.5 mg/ml in Tris buffer (0.05 Tris 0.2 M NaCl) pH 7.4, was dotted onto the nitrocellulose paper. A standard curve was made by diluting U-5 antibody 100 ug/ml to various concentrations. Nitrocellulose paper was immersed in 150 ul of a series of dilutions. Peroxidase labeled affinity purified antibody to mouse IgG + IgM (GAMIg) was used as second antibody and 4-CL-1-Naphthol as substrate.

B. Micro-ELISA test. The procedure used by the Dot method was used for micro ELISA except that 0-Phenylenediamine was used as a substrate and the absorbance at 492 nm was measured with a spectrophotometer. A standard curve for anti-BMP was prepared for analysis of serum samples containing unknown concentrations of BMP. For each assay the series of dilutions prepared for the standard curve was used to analyze the unknown sammles. A linear relationship with repect to anti-BMP was obtained when the correct dilution was selected and the dot method was designated for the range of 9 to 90 ng/ml. Above this range the sensitivity of the method declined along a plateau of over 100 ng/ml.

C. Assay for Serum Anti-BMP Human Antibody. 200 ul of human serum was diluted X 2 or from $10^{-1}$, $10^{-2}$, $10^{-3}$, $10^{-4}$, $10^{-5}$ as required. One ul of the solution of bBMP (100 ug/ml) was applied in dots to nitrocellulose paper. A Bio-Dot 96 well microfiltration apparatus was used to apply 150 ul to each well in five different antibody solutions. The intensity of the dye was estimated by analyses of additional samples serially diluted 1:2, 1:4, 1:16, 1:32, 1:64, 1:28, 1:256, until the color was undetectable to the human eye. The greatest dilution of serum of normal children detectable with the eye alone was selected 1:32 or 1:64. The procedure that followed was the same as was used for determination of bBMP in different animals, because (U-5) derived bovine anti-BMP cross-reacts with mouse, rabbit, and dog, and human.

The results are tabulated in Table VI below. ELISA-detected anti-BMP was found in relatively large concentrations in adults in which the levels of BMP were very low. In children in which the BMP levels were high, the levels of anti-BMP were relatively low, being less than a third found in adults. The anti-BMP levels in women with severe osteoporosis were about 2 times higher than in normal women of postmenopausal age, and about 2 to 15 times higher than women of premenopausal age. Anti-BMP antibody concentrations in serum, or the ratio of serum BMP:anti-BMP antibody were diagnostic of osteoporosis in the prefracture state.

TABLE VI

| | Relative Values ELISA of Anti-BMP | | |
|---|---|---|---|
| Subject | No. Patients | Sex | Anti-BMP ELISA. g/m |
| Adults | 8 | M | 21–66(69) |
| | 52 | F | 29–80(60) |
| Children | 10 | | 6–18(10) |

TABLE VI-continued

Relative Values ELISA of Anti-BMP

| Subject | No. Patients | Sex | Anti-BMP ELISA. g/m |
|---|---|---|---|
| Osteoporosis | 10 | | 79-106(14) |

Although the instant disclosure set forth all essential information in connection with the invention, the numerous publications cited herein may be of assistance in understanding the background of the invention and the state of the art. Accordingly, all of the publications cited are hereby incorporated by reference into the present disclosure.

It will be understood that this description and disclosure of the invention is intended to cover all changes and modifications of the invention which are within the spirit and scope of the invention.

What is claimed is:

1. A method for diagnosing bone disorder comprising the step of comparing the quantity of bone morphogenetic protein (BMP) in a test body fluid sample with the quantity of BMP in a control sample.

2. The method of claim 1, wherein the quantity of BMP in said test sample is determined by means of an immunoassay system.

3. The method of claim 2, wherein said test body fluid sample is serum.

4. The method of claim 3, wherein said immunoassay system is enzyme-linked-immunosorbent assay (ELISA).

5. The method of claim 3, wherein said bone disorder is selected from the group consisting of osteoporosis, Paget's disease and osteosarcoma.

6. The method of claim 5, wherein said immunoassay system is radioimmunoassay (RIA).

7. The method of claim 5, wherein said immunoassay system is enzyme-linked-immunosorbent assay (ELISA).

8. The method of claim 3, wherein said immunoassay system is radioimmunoassay (RIA).

9. The method of claim 2, wherein said bone disorder is selected from the group consisting of osteoporosis, Paget's disease and osteosarcoma.

10. The method of claim 9, wherein said immunoassay system is radioimmunoassay (RIA).

11. The method of claim 9, wherein said immunoassay system is enzyme-linked-immunosorbent assay (ELISA).

12. The method of claim 2, wherein said immunoassay system is radioimmunoassay (RIA).

13. The method of claim 2, wherein said immunoassay system is enzyme-linked-immunosorbent assay (ELISA).

14. The method of claim 1, wherein said test body fluid sample is serum.

15. The method of claim 14, wherein said bone disorder is selected from the group consisting of osteoporosis, Paget's disease and osteosarcoma.

16. The method of claim 1, wherein said bone disorder is selected from the group consisting of osteoporosis, Paget's disease and osteosarcoma.

17. A method of diagnosing bone disorder comprising the step of comparing the quantity of anti-bone morphogenetic protein (anti-BMP) antibody in a test body fluid sample with the quantity of anti-BMP antibody in a control sample.

18. The method of claim 17, wherein the quantity of anti-BMP antibody in said test sample is determined by means of an immunoassay system.

19. The method of claim 18, wherein said test body fluid sample is serum.

20. The method of claim 19, wherein said bone disorder is selected from the group consisting of osteoporosis, Paget's disease and osteosarcoma.

21. The method of claim 20, wherein said immunoassay system is radioimmunoassay (RIA).

22. The method of claim 20, wherein said immunoassay system is enzyme-linked-immunosorbent assay (ELISA).

23. The method of claim 19, wherein said immunoassay system is radioimmunoassay (RIA).

24. The method of claim 19, wherein said immunoassay system is enzyme-linked-immunosorbent assay (ELISA).

25. The method of claim 18, wherein said bone disorder is selected from the group consisting of osteoporosis, Paget's disease and osteosarcoma.

26. The method of claim 25, wherein said immunoassay system is radioimmunoassay (RIA).

27. The method of claim 25, wherein said immunoassay system is enzyme-linked-immunosorbent assay (ELISA).

28. The method of claim 18, wherein said immunoassay system is radioimmunoassay (RIA).

29. The method of claim 18, wherein said immunoassay system is enzyme-linked-immunosorbent assay (ELISA).

30. The method of claim 17, wherein said test body fluid is serum.

31. The method of claim 30, wherein said bone disorder is selected from the group consisting of osteoporosis, Paget's disease and osteosarcoma.

32. The method of claim 17, wherein said bone disorder is selected from the group consisting of osteoporosis, Paget's disease and osteosarcoma.

33. A method of diagnosing bone disorder, comprising the step of comparing the ratio of the quantity of bone morphogenetic protein (BMP) to the quantity of anti-bone morphogenetic protein (anti-BMP) antibody in a test body fluid sample with the ratio of the quantities in a control sample.

34. The method of claim 33, wherein the quantities of BMP and anti-BMP antibody in said test sample are determined by means of an immunoassay system.

35. The method of claim 34, wherein said test body fluid sample is serum.

36. The method of claim 35, wherein said bone disorder is selected from the group consisting of osteoporosis, Paget's disease and osteosarcoma.

37. The method of claim 36, wherein said immunoassay system is radioimmunoassay.

38. The method of claim 36, wherein said immunoassay system is enzyme-linked-immunosorbent assay (ELISA).

39. The method of claim 35, wherein said immunoassay system is radioimmunoassay.

40. The method of claim 35, wherein said immunoassay system is enzyme-linked-immunosorbent assay (ELISA).

41. The method of claim 34, wherein said bone disorder is selected from the group consisting of osteoporosis, Paget's disease and osteosarcoma.

42. The method of claim 41, wherein said immunoassay system is radioimmunoassay.

43. The method of claim 41, wherein said immunoassay system is enzyme-linked-immunosorbent assay (ELISA).

44. The method of claim 34, wherein said immunoassay system is radioimmunoassay.

45. The method of claim 34, wherein said immunoassay system is enzyme-linked-immunosorbent assay (ELISA).

46. The method of claim 33, wherein said test body fluid is serum.

47. The method of claim 46, wherein said bone disorder is selected from the group consisting of osteoporosis, Paget's disease and osteosarcoma.

48. The method of claim 33, wherein said bone disorder is selected from the group consisting of osteoporosis, Paget's disease and osteosarcoma.

* * * * *